(12) United States Patent
Noteborn et al.

(10) Patent No.: US 7,317,096 B1
(45) Date of Patent: Jan. 8, 2008

(54) APOPTIN-ASSOCIATING PROTEINS

(75) Inventors: Mathieu Hubertus Maria Noteborn, Leiden (NL); Astrid Adriana Anna Maria Danen-Van Oorschot, Berkell en Rodenrijs (NL)

(73) Assignee: Leadd B.V., Leiden (NL)

( * ) Notice: Subject to any disclaimer, the term of this patent is extended or adjusted under 35 U.S.C. 154(b) by 708 days.

(21) Appl. No.: 09/655,109

(22) Filed: Sep. 5, 2000

(30) Foreign Application Priority Data

Sep. 2, 1999 (EP) .................................. 99202858
Oct. 21, 1999 (EP) .................................. 99203465

(51) Int. Cl.
*C07H 21/04* (2006.01)
*C12N 15/85* (2006.01)
*C12N 15/63* (2006.01)

(52) U.S. Cl. .................... 536/23.1; 435/320.1; 435/325

(58) Field of Classification Search ............... 536/23.1, 536/23.4, 23.5
See application file for complete search history.

(56) References Cited

U.S. PATENT DOCUMENTS

| | | | |
|---|---|---|---|
| 5,981,205 | A | 11/1999 | Hemmings et al. |
| 6,809,189 | B2 | 10/2004 | Noteborn et al. |
| 6,878,692 | B2 | 4/2005 | Noteborn et al. |
| 2003/0105315 | A1 | 6/2003 | Specht et al. |

FOREIGN PATENT DOCUMENTS

| | | |
|---|---|---|
| EP | 0921192 A1 | 6/1999 |
| EP | 0924296 A2 | 6/1999 |
| WO | WO 96/41191 | 12/1996 |
| WO | WO 98/46760 | 10/1998 |
| WO | WO 99/08108 | 2/1999 |

OTHER PUBLICATIONS

Zhuang et al., Apoptin, a Protein Derived from Chicken Anemia Virus, Induces p53-independent Apoptosis in Human Osteosarcoma Cells, Cancer Res, Feb. 1995, pp. 486-489, vol. 55, No. 3.
Pietersen et al., Specific tumor-cell killing with adenovirus vectors containing the apoptin gene, Gene Therapy, 1999, pp. 882-892, vol. 6.
Bellamy, Christopher O.C., et al., "Cell death in health and disease: the biology and regulation of apoptosis," Seminars in Cancer Biology, vol. 6, pp. 3-16 (1995).
Danen-Van Oorschot, A.A.A.M., et al., "Apoptin induces apoptosis in human transformed and malignant cells but not in normal cells." Proc. Nat'l. Acad Sci. USA vol. 94, pp. 5843-5847 (May 1997).
Danen-van Oorschot, et al., A.A.A.M., "BAG-1 inhibits p53-induced but not apoptin-induced apoptosis," Apoptosis, vol. 2, No. 4, pp. 395-402 (1997).
Duke, Richard C., et al, "Cell Suicide in Health and Disease," Scientific American, pp. 80-87 (Dec. 1996).
Noteborn, M.H.M., et al., "A Single Chicken Anemia Virus Protein Induces Apoptosis," Journal of Virology, vol. 68, No. 1, pp. 346-351 (Jan. 1994).

Noteborn, M.H.M., et al., "Characterization of Cloned Chicken Anemia Virus DNA That Contains All Elements for the Infectious Replication Cycle." Journal of Virology, vol. 65, No. 6, pp. 3131-3139 (Jun. 1991).
Noteborn, Mathieu H.M., et al, "Chicken Anemia Virus Induction of Apoptosis by a Single Protein of a Single-Stranded DNA Virus," Seminars in Virology. vol. 8, pp. 497-504 (1998).
Noteborn, Mathieu H.M., et al., "Simultaneous expression of recombinant baculovirus-encoded chicken anaemia virus (CAV) proteins VP1 and VP2 is required for formation of the CAV-specific neutralizing epitope," Journal of General Virology, vol. 79, pp. 3073-3077 (1998).
Paulovich, Amanda G., et al, "When Checkpoints Fail," Cell, vol. 88, pp. 315-321 (Feb. 7, 1997).
Steller Hermann, "Mechanims and Genes of Cellular Suicide," Science, vol. 267, pp. 1445-1449 (Mar. 10, 1995).
Teodoro, Jose G, et al, "Regulation of Apoptosis by Viral Gene Products," Journal of Virology, vol. 71, No. 3, pp. 1739-1746 (Mar. 1997).
Thompson, Craig B, "Apoptosis in the Pathogenesis and Treatment of Disease," Science, vol. 267, pp. 1456-1462 (Mar. 10, 1995).
Strausberg, Robert, "qy85c09.x1 NCI_CGAP_Brn25 *Homo sapiens* cDNA clone Image:2018800 3', mRNA sequence," Jan. 7, 1999, Accession No. AI360308.
Zhao S., "Use of BAC End Sequences from Library RPCI-11 for Sequence-Ready Map building," Mar. 15, 1999, Accession No. AQ382839.
Strausberg, Robert, "wd70d04.x1 NCI_CGAP_Lu24 *Homo sapiens* cDNA clone Image:2336935 3', mRNA sequence," Jun. 3, 1999, Accession No. AI692778.
Benet et al., pp. 3-32, in The Pharmacological Basis of Therapeutics, 8th ed., McGraw-Hill, Inc., New York, 1990.
Jain et al., Vascular and interstitial barriers to delivery of therapeutic agents in tumors, Cancer and Metastasis Reviews, 1990, pp. 253-266, vol. 9.
Jain R.K, Delivery of Molecular Medicine to Solid Tumors, 1996, Science, pp. 1079-1080, vol. 271.
Dermer, Another Anniversary for the War on Cancer, Biotechnology, 1994, pp. 320, vol. 12.
Database GenEmbl on GenCore version 4.5, Accession No. AX015052, Oct. 1999.
Strausberg R. Database EST on GenCore version 4.5, Accession No. BE746443, Sep. 2000.
Danen-Van Oorschot et al., BCL-2 Stimulated Apoptin-induced Apoptosis, pp. 245-249 in Drug Resistance in Leukemia and Lymphoma III, ed. Kaspers et al., Kluwer Academic/Plenum Publishers, New York, 1999.

(Continued)

*Primary Examiner*—Sumesh Kaushal
*Assistant Examiner*—David A. Montanari
(74) *Attorney, Agent, or Firm*—TraskBritt (57) ABSTRACT

The invention relates to the field of apoptosis. The invention provides novel therapeutic possibilities, for example novel combinatorial therapies or novel therapeutic compounds that can work alone, sequentially to, or jointly with apoptin, especially in those cases wherein p53 is (partly) non-functional.

10 Claims, 4 Drawing Sheets

OTHER PUBLICATIONS

Noteborn et al., Apoptin-induced apoptosis: potential for antitumor therapy, Drug Resistance Updates, 1998, pp. 99-103, vol. 1.

Noteborn et al., Apoptin induces apoptosis in transformed cells specifically: Potentials for an antitumor therapy, Biogenic Amines, 1998, pp. 73-91, vol. 15, No. 1.

Abstract XP-002140967, May 1999.

Abstract XP-002140968, May 1995.

Abstract XP-002140969, 2000.

McDonnell et al., "Implications of apoptotic cell death regulation in cancer therapy," Cancer Biology, 1995, pp. 53-60, vol. 6.

Mullersman et al., "The PHD finger: implications for chromatin-mediated transcriptional regulation," TIBS Feb. 20, 1995, pp. 56-59.

Jacobson et al., "Modifying chromatin and concepts of cancer," Chromosomes and expression mechanisms, pp. 175-184.

Lu et al., "A Novel Gene (PLU-1) Containing Highly Conserved Putative DNA/Chromatin Binding Motifs Is Specifically Up-regulated in Breast Cancer," The Journal of Biological Chemistry, 1999, pp. 15633-15645, vol. 274, No. 22.

Zhuang et al., "Apoptin, a Protein Encoded by Chicken Anemia Virus, Induces Cell Death in Various Human Hematologic Malignant Cells in vitro," Leukemia, vol. 9, Suppl. 1, pp. S118-S120, 1995.

Danen-Van Oorschot, et al. (1997) "Apoptin induces apoptosis in human transformed and malignant cells but not in normal cells." *Proc Natl Acad Sci, USA*: 94, 5843-5847.

Danen-Van Oorschot, et al. (1997) "BAG-1 inhibits p53-induced but not apoptin-induced apoptosis." *Apoptosis* 2, 395-402.

Garcia, et al. (1999) "RYBP, a new repressor protein that interacts with components of the mammalian polycomb complex, and with the transcription factor YY1." *EMBO J* 18, 3404-3418.

Kerr, et al. (1994) "Apoptosis: Its significance in cancer and cancer therapy." *Cancer* 73, 2013-2026.

Levine, A.J. (1997) "p53, the cellular gatekeeper for growth and division." *Cell* 88, 323-331.

Noteborn, et al. (1991) "Characterization of cloned chicken anemia virus DNA that contains all elements for the infectious replication cycle." *J Virol* 65, 3131-3139.

Noteborn, et al. (1994) "A single chicken anemia virus protein induces apoptosis." *J Virol* 68, 346-351.

Noteborn, et al. (1998) "Chicken anemia virus: Induction of apoptosis by a single protein of a single-stranded DNA virus." *Seminars in Virology* 8, 497-504.

Paulovich, et al. (1997) "When checkpoints fail." *Cell* 88, 315-321.

Pietersen et al. (1999) "Specific tumor-cell killing with adenovirus vectors containing the apoptin gene." *Gene Therapy* 6, 882-892.

Zhuang, et al. (1995) "Apoptin, a protein derived from chicken anemia virus, induces a p53-independent apoptosis in human osteosarcoma cells." *Cancer Research* 55, 486-489.

```
                                            XhoI
  1    ACCANACCCAAAAAAAGAGATCTGGAATTCGGATCCTCGAGGCCACGAAGGCCGAAACAG

61    TGCTGAAGCCTTTAAATGCAGCATCTGCGATGTGAGGAAAGGCACCTCCACCAGAAAACC

121    TCGGATCAATTCTCAGCTGGTGGCNCAACAAGTGGCACAACAGTATGCCACCCCACCACC

181    CCCTAAAAAGGAGAAGAAGGAGAAAGTTGAAAAGCAGGACAAAGAGAAACCTGAGAAAGA

241    CAAGGAAATTAGTCCTAGTGTTACCAAGAAAAATACCAACAAGAAAACCAAACCAAAGTC

301    TGACATTCTGAAAGATCCTCCTAGTGAAGCAAACAGCATACAGTCTGCAAATGCTACAAC

361    AAAGACCAGCGAAACAAATCACACCTCAAGGCCCCGGCTGAAAAACGTGGACAGGAGCAC

421    TGCACAGCAGTTGGCAGTAACTGTGGGCAACGTCACCGTCATTATCACAGACTTTAAGGA

481    AAAGACTCGCTCCTCATCGACATCCTCATCCACAGTGACCTCCAGTGCAGGGTCAGAACA

541    GCAGAACCAGASCAGCTCGGGGTCAGAGAGCACAGACAAGGGCTCCTCCCGTTCCTCCAC

601    GCCAAAGGGCGACATGTCAGCAGTCAATGATGAATCTTTCTGAAATTGCACATGGAATTG

661    TGAAAACTATGAATCAGGGTATGAAATTCAAAACCTCCACCTGCCCATGCTGCTTGCATC

721    CCTGGAGAATCTTCTGTGGACATCGACCTCTTAGTGATGCTGCCAGGATAATTTCTGCTT

781    GCCATGGGCATCTGGCCACCAAGGAATTTCGCACCCTGACGATTACTCTTGACACTTTTA

841    TGTATTCCATTGTTTTATATGATTTTCCTAACAATCATTTATAATTGGATGTGCTCCTGA
                                            XhoI
901    ATCTACTTTTTATAAAAAAAGCCTTYGTGGCCTCGAGAGATCTATGA
```

FIG. 1

| | |
|---|---|
| 1 | TATAACTATCTATTCGATGATGAAGATACCCCACCAAACCCAAAAAAAGAGATCTGGAAT |
| | XhoI |
| 61 | TCGGATCCTCGAGGCCACGAAGGCCTTTCTCCTCCGAGCGGCGCCGGTTTCGGCTTGGGG |
| 121 | GGGGCGGGGTACAGCCCATCCATGACCATGGGCGACAAGAAGAGCCCGACCAGGCCAAAA |
| 181 | AGACAAGCGAAACCTGCCGCAGACGAAGGGTTTTGGGATTGTAGCGTCTGCACCTTCAGA |
| 241 | AACAGTGCTGAAGCCTTTAAATGCAGCATCTGCGATGTGAGGAAAGGCACCTCCACCAGA |
| 301 | AAACCTCGGATCAATTCTCAGCTGGTGGCACAACAAGTGGCACAACAGTATGCCACCCCA |
| 361 | CCACCCCCTAAAAAGGAGAAGAAGGAGAAAGTTGAAAAGCAGGACAAAGAGAAACCTGAG |
| 421 | AAAGACAAGGAAATTAGTCCTAGTGTTACCAAGAAAAATACCAACAAGAAAACCAAACCA |
| 481 | AAGTCTGACATTCTGAAAGATCCTCCTAGTGAAGCAAACAGCATACAGTCTGCAAATGCT |
| 541 | ACAACAAAGACCAGCGAAACAAATCACACCTCAAGGCCCCGGCTGAAAAACGTGGACAGG |
| 601 | AGCACTGCACAGCAGTTGGCAGTAACTGTGGGCAACGTCACCGTCATTATCACAGACTTT |
| 661 | AAGGAAAAGACTCGCTCCTCATCGACATCCTCATCCACAGTGACCTCCAGTGCAGGGTCA |
| 721 | GAACAGCAGAACCAGAGCAGCTCGGGGTCAGAGAGCACAGACAAGGGCTCCTCCCGTTCC |
| 781 | TCCACGCCAAAGGGCGACATGTCAGCAGTCAATGATGAATCTTTGTGAAATTGCACATGG |
| 841 | AATTGTGAAAACTATGAATCAGGGTATGAAATTCAAAACCTCCACCTGCCCATGCTGCTT |
| 901 | GCATCCCTGGAGAATCTTCTGTGGACATCGACCTCTTAGTGATGCTGCCAGGATAATTTC |
| 961 | TGCTTGCCATGGGCATCTGGCCACCAAGGAATTTCGCACCCTGACGATTACTCTTGACAC |
| 1021 | TTTTATGTATTCCATTGTTTTATATGATTTTCCTAACAATCATTTATAATTGGATGTGCT |
| | XhoI |
| 1081 | CCTGAATCTACTTTTTATAAAAAGGCCTTCGTGGCCTCGAGAGATCTATGA |

FIG. 2

```
1    HEGLSPPSGA  GFGLGGAGYS  PSMTMGDKKS  PTRPKRQAKP
41   AADEGFWDCS  VCTFRNSAEA  FKCSICDVRK  GTSTRKPRIN
81   SQLVAQQVAQ  QYATPPPPKK  EKKEKVEKQD  KEKPEKDKEI
121  SPSVTKKNTN  KKTKPKSDIL  KDPPSEANSI  QSANATTKTS
161  ETNHTSRPRL  KNVDRSTAQQ  LAVTVGNVTV  IITDFKEKTR
201  SSSTSSSTVT  SSAGSEQQNQ  SSSGSESTDK  GSSRSSTPKG
241  DMSAVNDESF  *NCTWNCENY  ESGYEIQNLH  LPMLLASLEN
281  LLWTSTS**C  CQDNFCLPWA  SGHQGISHPD  DYS*HFYVFH
321  CFI*FS*QSF  IIGCAPESTF  YKKAFVASRD  L*
```

APOPTIN-ASSOCIATING PROTEINS

This application claims priority from European Application number EP 99202858.9 (Sep. 2, 1999) and European Application number EP 99203465.2 (Oct. 21, 1999).

TECHNICAL FIELD

The invention relates to the field of biotechnology, more specifically to apoptosis, or cell-death.

BACKGROUND OF THE INVENTION

Apoptosis is an active and programmed physiological process for eliminating superfluous, altered or malignant cells (Earnshaw, 1995, Duke et al., 1996). Apoptosis is characterized by shrinkage of cells, segmentation of the nucleus, condensation and cleavage of DNA into domain-sized fragments, in most cells followed by internucleosomal degradation. The apoptotic cells fragment into membrane-enclosed apoptotic bodies. Finally, neighbouring cells and/or macrophages will rapidly phagocytose these dying cells (Wyllie et al., 1980, White, 1996). Cells grown under tissue-culture conditions and cells from tissue material can be analyzed for being apoptotic with agents staining DNA, such as DAPI, which stains normal DNA strongly and regularly, whereas apoptotic DNA is stained weakly and/or irregularly (Noteborn et al., 1994, Telford et al., 1992).

The apoptotic process can be initiated by a variety of regulatory stimuli (Wyllie, 1995, White 1996, Levine, 1997). Changes in the cell survival rate play an important role in human pathogenesis of diseases, e.g., in cancer development and auto-immune diseases, where enhanced proliferation or decreased cell death is observed (Kerr et al., 1994, Paulovich, 1997). A variety of chemotherapeutic compounds and radiation have been demonstrated to induce apoptosis in tumor cells, in many instances via wild-type p53 protein (Thompson, 1995, Bellamy et al., 1995, Steller, 1995, McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994, Sachs and Lotem, 1997).

For such tumors lacking functional p53 (representing more than half of the tumors) alternative anti-tumor therapies are under development based on induction of apoptosis independent of p53 (Thompson 1995, Paulovich et al., 1997). One has to search for the factors involved in induction of apoptosis, which do not need p53 and/or can not be blocked by anti-apoptotic activities, such as Bcl-2 or Bcr-abl-like. These factors might be part of a distinct apoptosis pathway or might be (far) downstream of the apoptosis inhibiting compounds.

Apoptin is a small protein derived from chicken anemia virus (CAV; Noteborn and De Boer, 1995, Noteborn et al., 1991, Noteborn et al., 1994; 1998a), which can induce apoptosis in human malignant and transformed cell lines, but not in untransformed human cell cultures. In vitro, apoptin fails to induce programmed cell death in normal lymphoid, dermal, epidermal, endothelial and smooth-muscle cells. However, when normal cells are transformed they become susceptible to apoptosis by apoptin. Long-term expression of apoptin in normal human fibroblasts revealed that apoptin has no toxic or transforming activity in these cells (Danen-van Oorschot, 1997 and Noteborn, 1996).

In normal cells, apoptin was found predominantly in the cytoplasm, whereas in transformed or malignant cells, i.e., characterized by hyperplasia, metaplasia, dysplasia or aplasia, it was located in the nucleus, suggesting that the localization of apoptin is related to its activity (Danen-van Oorschot et al. 1997). Apoptin-induced apoptosis occurs in the absence of functional p53 (Zhuang et al., 1995a), and cannot be blocked by Bcl-2, Bcr-abl (Zhuang et al., 1995), or the Bcl-2-associating protein BAG-1 (Danen-Van Oorschot, 1997a, Noteborn, 1996).

Therefore, apoptin is a therapeutic compound for the selective destruction of tumor cells, or other hyperplasia, metaplasia, or dysplasia, especially for those tumor cells which have become resistant to (chemo)-therapeutic induction of apoptosis, due to the lack of functional p53 and (over)-expression of Bcl-2 and other apoptosis-inhibiting agents (Noteborn and Pietersen, 1998). It appears, that even pre-malignant, minimally transformed cells, are sensitive to the death-inducing effect of apoptin. In addition, Noteborn and Zhang (1998) have shown that apoptin-induced apoptosis can be used for diagnosis of cancer-prone cells and treatment of cancer-prone cells.

The fact that apoptin does not induce apoptosis in normal human cells, at least not in vitro, shows that a toxic effect of apoptin treatment in vivo will be very low. Noteborn and Pietersen (1998) and Pietersen et al. (1998) have provided evidence that adenovirus expressed apoptin does not have an acute toxic effect in vivo. In addition, in nude mice it was shown that apoptin has a strong anti-tumor activity.

However, to further enlarge the array of therapeutic anti-cancer or anti-auto-immune-disease compounds available in the art, additional therapeutic compounds are desired that are designed to work alone, sequentially to, or jointly with apoptin, especially in those cases wherein p53 is (partly) non-functional.

SUMMARY OF THE INVENTION

The invention provides novel therapeutic possibilities, for example novel combinational therapies or novel therapeutic compounds that can work alone, sequentially to, or jointly with apoptin, especially in those cases wherein p53 is (partly) non-functional.

In a first embodiment, the invention provides an isolated or recombinant nucleic acid or functional equivalent or fragment thereof encoding an apoptin-associating proteinaceous substance capable of providing apoptosis, alone or in combination with other apoptosis inducing substances, such as apoptin. Proteinaceous substance herein is defined as a substance comprising a peptide, polypeptide or protein, optionally having been modified by for example glycosylation, myristilation, phosphorylation, the addition of lipids, by homologous or heterologous di-or multimerization, or any other (posttranslational) modifications known in the art.

Apoptin-associating herein is defined as belonging to the cascade of substances specifically involved in the cascade of events found in the apoptosis pathway as inducible by apoptin, preferably those substances that are specifically involved in the p53-independent apoptosis pathway.

BRIEF DESCRIPTION OF THE FIGURES

FIG. 3 shows the amino-acid sequence of the analyzed region of the apoptin-associating clone AAP-1-b (bold). In addition, the three C-terminal amino acids H—E—G of the multiple cloning site of pACT are given to illustrate that the AAP-1 amino acid sequence is in frame with the GAL4-activation domain. (SEQ ID NO:6) This feature proves that the AAP-1 region is indeed synthesized in yeast cells. Note that in FIG. 3 amino acid position 23 corresponds with the first amino acid of an AAP-1 like protein. Functional domains or fragments herein can for example be identified as a transcription factor binding domain running from amino acid position 1 (=23 in FIG. 3) to about 54; a zinc-finger motive, protein—protein interaction and/or protein-nucleic acid interaction domain running from about amino acid position 25 (=47 in FIG. 3) to about 42; an apoptosis associated region running from about amino acid position 32 to 226; a nuclear localization signal running from about amino acid position 74 to 81; and a nuclear localization signal running from about amino acid position 102 to 108, or at equivalent positions in another AAP-1 like protein.

BRIEF DESCRIPTION OF THE PREFERRED EMBODIMENTS

In a preferred embodiment, the invention provides an isolated or recombinant nucleic acid or functional equivalent or fragment thereof encoding an apoptin-associating proteinaceous substance capable of providing apoptosis. More preferably the encoded apoptin-associated proteinaceous substance co-localizes with other apoptosis inducing substances, for example apoptin, when the two apoptosis inducing substances are present in the same cell. In normal non-transformed cells the two apoptosis inducing proteins co-localize in the cytoplasm whereas in transformed or malignant cells the two apoptosis-inducing proteins co-localizes in the nucleus. In another embodiment the apoptin-associating substance is capable of binding to the mouse transcription factor YY1, which was earlier shown to bind to the mouse AAP-1 homologue RYBP (Garcia et al., 1999). In a most preferred embodiment the isolated or recombinant nucleic acid or functional equivalent or fragment thereof encoding an apoptin-associating proteinaceous substance capable of providing apoptosis is derived from a cDNA library, preferably a vertebrate cDNA library, such as derivable from poultry, but more preferably a mammalian cDNA library, preferably wherein said cDNA library comprises human cDNA.

Figure 1:
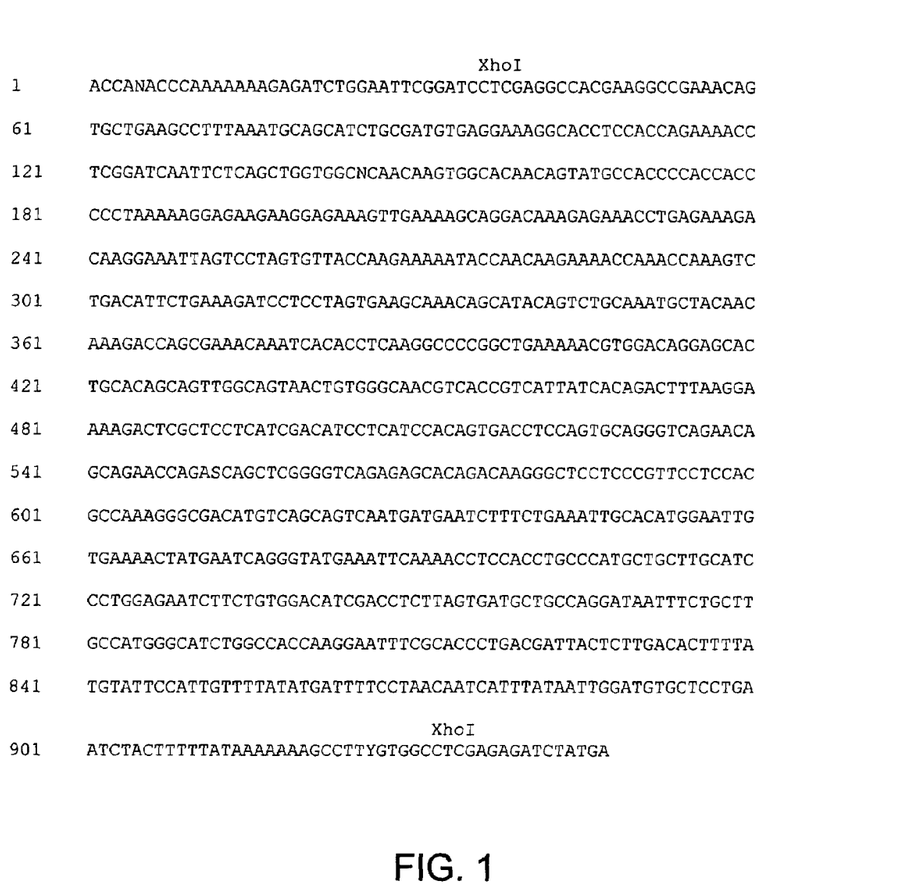
FIG. 1 shows the partial sequence of vector pMT2SM-AAP-1-a (SEQ ID NO:4). The DNA sequence of the AAP-1-a cDNA is given in bold.
Figure 2:
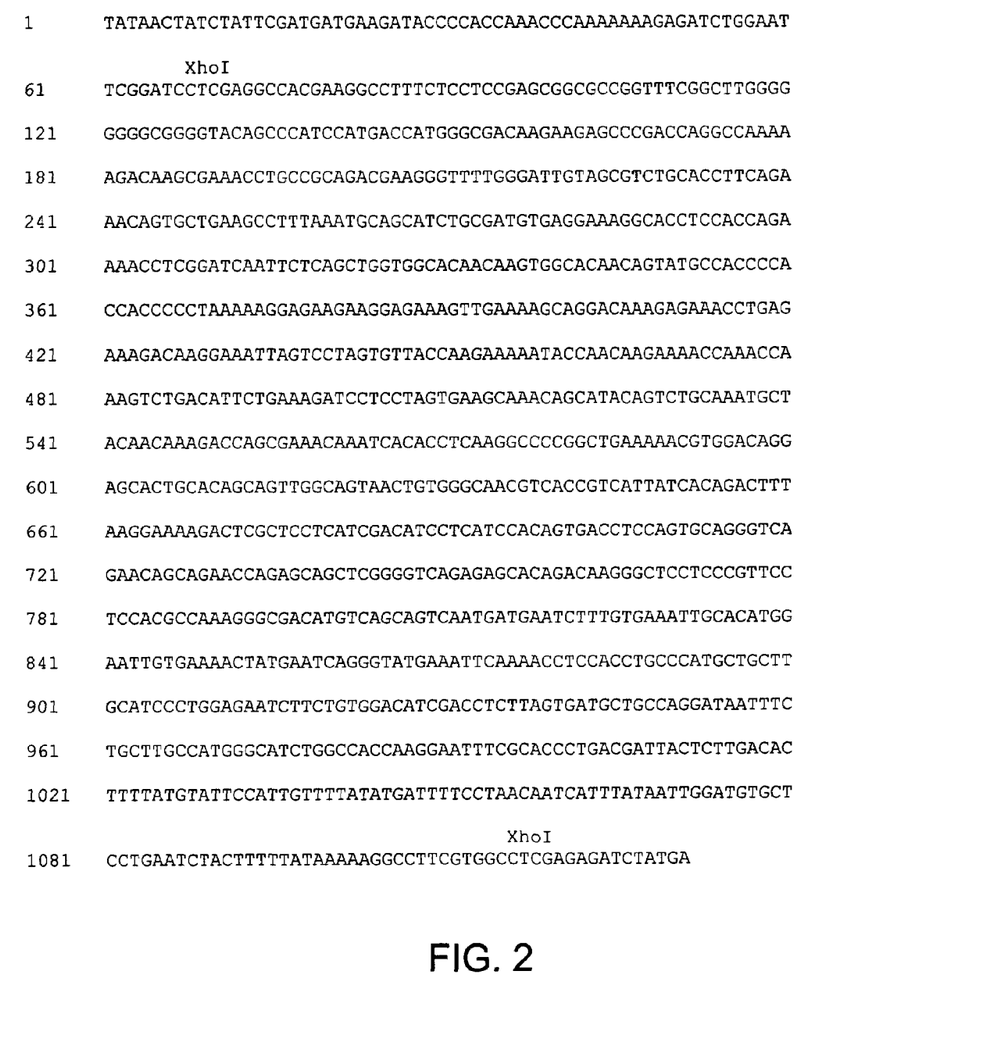
FIG. 2 shows the partial sequence of vector pMT2SM-AAP-1-b. The DNA sequence of the AAP-1-b cDNA is given in bold. (SEQ ID NO:5)

In another embodiment, the invention provides an isolated or recombinant nucleic acid or functional equivalent or fragment thereof encoding an apoptin-associating proteinaceous substance capable of providing apoptosis capable of hybridizing to a nucleic acid molecule encoding an apoptin-associating proteinaceous substance capable of providing apoptosis as shown in FIG. 1 or 2, in particular encoding a novel protein capable of providing apoptosis or functional equivalent or functional fragment thereof called apoptin-associating protein 1, abbreviated herein also as AAP-1. Of course, an isolated or recombinant nucleic acid or functional equivalent or fragment thereof encoding an additional apoptin-associating proteinaceous substance capable of associating with the AAP-1 protein are herewith also provided, means and methods to arrive at such an additional protein located in the apoptin cascade follow those of the detailed description given herein.

In particular, the invention provides an isolated or recombinant nucleic acid or functional equivalent or fragment thereof encoding an apoptin-associating proteinaceous substance capable of providing apoptosis being at least 70% homologous, preferably at least 80%, more preferably at least 90%, most preferably at least 95% homologous to a nucleic acid molecule, or to a functional equivalent or functional fragment thereof, encoding an apoptin-associating proteinaceous substance as shown in FIG. 1 or 2.

Furthermore, the invention provides a vector comprising a nucleic acid according to the invention. Examples of such a vector are given in the detailed description given herein; such as vector pMT2SM-AAP-1-a or b, pMT2SM vector expressing Myc-tagged AAP-1-a or AAP-1-b cDNAs, a plasmid expressing an apoptin-associating protein fragment, *E. coli* overexpression vectors such as pMAL and pET22b comprising a nucleic acid according to the invention and so on. These and other vectors are for example useful in finding additional apoptin-associating proteinaceous substances from the cascade, as defined above, or for the (over)expression of a protein encoded by a nucleic acid according to the invention.

In yet another embodiment, the invention provides a vector comprising a nucleic acid according to the invention, said vector comprising a gene-delivery vehicle, making the invention very useful in gene therapy. By equipping a gene delivery vehicle with a nucleic acid according to the invention, and by targeting said vehicle to a cell or cells that have been over-proliferating and/or have shown decreased death rates, said gene delivery vehicle provides said cell or cells with the necessary means for apoptosis, providing far reaching therapeutic possibilities.

Furthermore, the invention provides a host cell comprising a nucleic acid or a vector according to the invention. Examples comprise transformed or transfected bacterial or yeast cells as described in the detailed description herein. Preferred is a host cell according to the invention which is a transformed eukaryotic cell such as a yeast cell or a vertebrate cell, such as mammalian or Cos cells transformed or transfected with a nucleic acid or vector according to the invention. Said cells are in general capable to express or produce a proteinaceous substance capable of providing apotosis with the ability to associate with apoptin.

The invention furthermore provides an isolated or recombinant apoptin-associating proteinaceous substance capable of providing apoptosis. As for example shown herein in FIG. 4, expression of such apoptin-associating proteinaceous substance in cells, such as tumour cells, or other over-proliferating cells, induces the apoptic process. It can do so alone, or in the presence of other apoptosis inducing substances such as apoptin, and especially so independent of p53, showing that also in those cases where (functional) p53 is absent apoptosis can be induced by a substance according to the invention. When the apoptin-associated proteinaceous substance capable of providing apoptosis is used together with another apoptosis inducing substance, for example apoptin, the two proteinaceous substances co-localize in the cytoplasm of normal cells and do not result in apoptosis.

Figure 3:
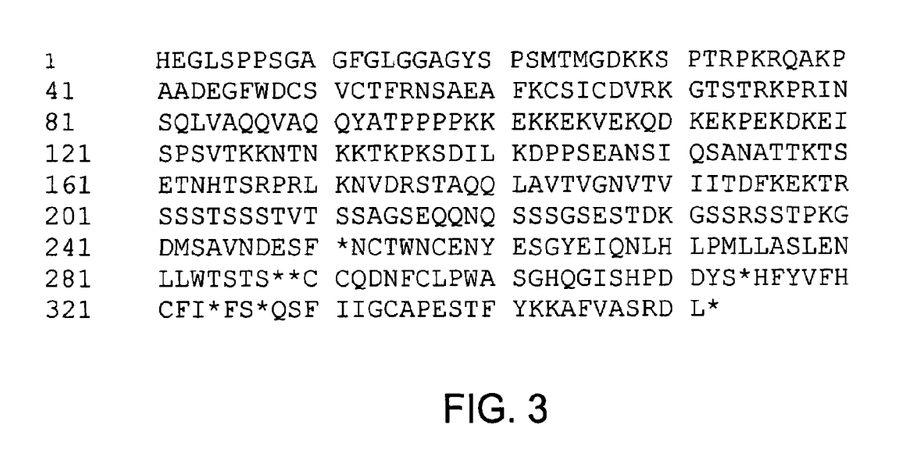

Whereas in transformed or malignant cells the two apoptosis-inducing proteins co-localize in the nucleus and induce apoptosis. The invention also provides a proteinaceous substance according to the invention which binds to the transcription factor YY1, which was already shown to bind the AAP-1 mouse homologue RYBP. In particular, the invention provides a proteinaceous substance according to the invention encoded by a nucleic acid according to the invention, for example comprising at least a part of an amino acid sequence as shown in FIG. 3 or a functional equivalent or functional fragment thereof capable of providing apoptosis alone or in combination with other apotosis inducing substances such as apoptin.

The invention also provides an isolated or synthetic antibody specifically recognizing a proteinaceous substance or functional equivalent or functional fragment thereof according to the invention. Such an antibody is for example obtainable by immunizing an experimental animal with a apoptin-associating proteinaceous substance or an immunogenic fragment or equivalent thereof and harvesting polyclonal antibodies from said immunized animal (as shown herein in the detailed description), or obtainable by other methods known in the art such as by producing monoclonal antibodies, or (single chain) antibodies or binding proteins expressed from recombinant nucleic acid derived from a nucleic acid library, for example obtainable via phage display techniques.

With such an antibody, the invention also provides a proteinaceous substance specifically recognizable by such an antibody according to the invention, for example obtainable via immunoprecipitation, Western Blotting, or other immunological techniques known in the art.

Figure 4:
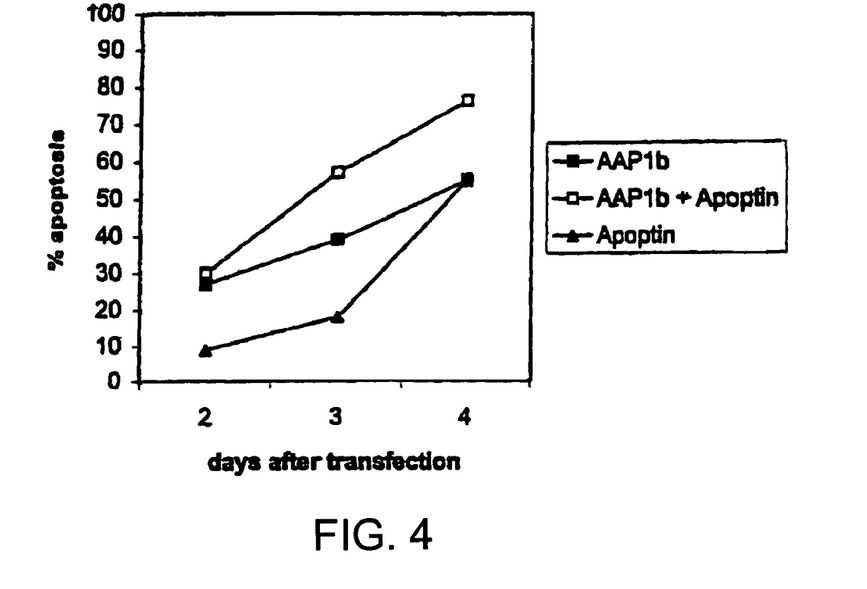
FIG. 4 shows the apoptotic activity of AAP-1-b protein in Saos-2 cells, when expressed alone (filled square) or in combination with apoptin (open square). The percentage of apoptin-induced apoptosis is also indicated (filled triangle).

Furthermore, the invention provides use of a nucleic acid, vector, host cell, or proteinaceous substance according to the invention for the induction of apoptosis, as for example shown in FIG. 4. In particular, such use is provided wherein said apoptosis is p53-independent. In particular, such use is also provided further comprising use of a nucleic acid encoding apoptin or a functional equivalent or fragment thereof or use of apoptin or a functional equivalent or fragment thereof. As can be seen from FIG. 4, combining these apoptin-inducing substances increases the percentage apoptosis of treated tumour cells.

Such use as provided by the invention is particularly useful from a therapeutic viewpoint. The invention provides herewith a pharmaceutical composition comprising a nucleic acid, vector, host cell, or proteinaceous substance according to the invention. In addition, such a pharmaceutical composition according to the invention further comprises a nucleic acid encoding apoptin or a functional equivalent or fragment thereof or apoptin or a functional equivalent or fragment thereof.

Such a pharmaceutical composition is in particular provided for the induction of apoptosis, for example wherein said apoptosis is p53-independent, for the treatment of a disease where enhanced cell proliferation or decreased cell death is observed, as is in general the case when said disease comprises cancer or auto-immune disease. Herewith the invention provides a method for treating an individual carrying a disease where enhanced cell proliferation or decreased cell death is observed comprising treating said individual with a pharmaceutical composition according to the invention. In particular these compositions comprise a factor of an apoptosis pathway, which is specific for transformed cells. Therefore, these compositions are essential for new treatments, but also for diagnosis of diseases related with aberrancies in the apoptotic process, such as cancer and auto-immune diseases.

In the field of diagnosis the invention provides a method for detecting the presence of cancer cells or cells that are cancer prone in a sample of cells comprising transfecting cells in said sample with a nucleic acid or a vector according to the invention culturing said cells and determining the percentage of apoptosis of cells in said sample. For example, we can conclude that the cellular localization of AAP-1 is different in tumorigenic/transformed cells in comparison to normal non-transformed cells. Furthermore, accumulation of AAP-1 in the nucleus correlates with apoptosis induction, whereas cytoplasmic localization correlates with cell viability and normal proliferative capacity. The invention thus provides a method for detecting the presence of cancer cells or cells that are cancer prone in a sample of cells comprising transfecting cells in said sample with a nucleic acid or a vector according to the invention and determining the intracellular localization of a proteinaceous substance derived from said nucleic acid or vector in cells in said sample. In particular, the invention provides a method wherein the presence of said proteinaceous substance in said cells is detected by immunostaining said cells with an antibody, such as with an immunofluorescence assay, or an other immunoassay known in the art. Preferably, said antibody comprises an antibody according to the invention.

Also, the invention provides a method for identifying a putative cancer-inducing agent, such as transforming genes or functional fragments thereof comprising exposing a sample of cells to said agent, for example by transfection, or by merely providing the agent to the medium surrounding the cells, and detecting the presence of cancer cells or cells that are cancer prone in a sample of cells with a method according to the invention.

In addition, the invention provides a method to detect cancer-proneness of a sample of cells, and thereby to detect cancer-proneness of the individual from which those cells were sampled, comprising submitting said cells to a cancer-inducing agent, such as UV-light, and detecting the presence of cancer cells or cells that are cancer prone in a sample of cells with a method according to the invention.

The invention will be explained in more detail in the following detailed description which does not limit the invention.

EXPERIMENTAL

We have used the yeast-2 hybrid system (Durfee et al., 1993) to identify apoptin-associating cellular compounds, which are essential in the induction of apoptosis. The system uses an in vivo strategy to identify human proteins capable of physically associating with apoptin. It has been used to screen cDNA libraries for clones encoding proteins capable of binding to a protein of interest (Fields and Song, 1989, Yang et al., 1992). The invention provides, for example, a novel apoptin-associating protein, one of which is named apoptin-associating protein 1, abbreviated as AAP-1. The invention also provides a method for inducing apoptosis through interference with the function of this newly discovered AAP-1 protein or functional equivalents or fragments thereof and/or the induction of apoptosis by means of (over)expression of AAP-1 or related gene or functional equivalents or fragments thereof.

The invention also provides an anti-tumor therapy based on the interference with the function of AAP-1-like proteins and/or its (over)expression. AAP-1-like proteins are normally not very abundant in immortalized cell lines. Therefore, an aberrant high level of AAP-1-like proteins will result in the induction of the opposite process of cell transformation, namely apoptosis. The invention furthermore provides the mediator of apoptin-induced apoptosis, which is tumor-specific. The invention provides a therapy for cancer, auto-immune diseases or related diseases which is based on AAP-1-like proteins alone or in combination with apoptin and/or apoptin-like compounds.

Materials and Methods

Construction of pGBT9-VP3

For the construction of the bait plasmid, which enables the identification of apoptin-associating proteins by means of a yeast-two-hybrid system, plasmid pET-16b-VP3 (Noteborn unpublished results) was treated with NdeI and BamHI. The 0.4 kb NdeI BamHI DNA fragment was isolated from low-melting-point agarose. GAL4-activation domain-tagged cDNA library.

The expression vector pACT, containing the cDNAs from Epstein-Barr-virus-transformed human B cells fused to the GAL4 transcriptional activation domain, was used for detecting apoptin-associating proteins. The pACT cDNA library is derived from the lambda-ACT cDNA library, as described by Durfee et al. 1993.

Bacterial and Yeast Strains

The *E. coli* strain JM109 was the transformation recipient for the plasmid pGBT9 and pGBT-VP3. The bacterial strain electromax/DH10B was used for the transformation needed for the recovery of the apoptin-associating pACT-cDNAs, and was obtained from GIBCO-BRL, USA.

The yeast strain Y190 was used for screening the cDNA library, and all other transformations, which are part of the yeast-two-hybrid system.

Media

For drug selections Luria Broth (LB) plates for *E. coli* were supplemented with ampicillin (50 microgram per ml). Yeast YPD and SC media were prepared as described by Rose et al. (1990).

Transformation of competent yeast strain Y190 with plasmids pGBT-VP3 and pACT-cDNA and screening for beta-galactosidase activity.

The yeast strain Y190 was made competent and transformed according to the methods described by Klebe et al. (1983). The yeast cells were first transformed with pGBT-VP3 and subsequently transformed with pACT-cDNA, and these transformed yeast cells were grown on histidine-minus plates, also lacking leucine and tryptophan.

Hybond-N filters were layed on yeast colonies, which were histidine-positive and allowed to wet completely. The filters were lifted and submerged in liquid nitrogen to permeabilize the yeast cells. The filters were thawed and placed with the colony side up on Whattman 3MM paper in a petridish with Z-buffer (Per liter: 16.1 gr $Na_2HPO_4.7H_2O$, 5.5 gr $NaH_2PO_4.H_2O$, 0.75 gr KCl and 0,246 gr $MgSO_4.7H_2O$, pH 7.0) containing 0.27% beta-mercapto-ethanol and 1 mg/ml X-gal. The filters were incubated for at least 15 minutes or during night.

Recovery of Plasmids from Yeast

Total DNA from yeast cells, which were histidine- and beta-galactosidase-positive, was prepared by using the glusulase-alkaline lysis method as described by Hoffman and Winston (1987) and used to transform Electromax/DH10B bacteria via electroporation using a Bio-Rad GenePulser according the manufacturer's specifications.

Transformants were plated on LB media containing the antibiotic agent ampicillin.

Isolation of Apoptin-Associating pACT Clones

By means of colony-filter assay the colonies were lysed and hybridized to a radioactive-labeled 17-mer oligomer, which is specific for pACT (see also section Sequence analysis). Plasmid DNA was isolated from the pACT-clones, and by means of XhoI digestion analyzed for the presence of a cDNA insert.

Sequence Analysis

The subclones containing the sequences encoding apoptin-associating proteins were sequenced using dideoxy NTPs according to the Sanger-method, which was performed by Eurogentec, Seraing, Belgium). The used sequencing primer was a pACT-specific 17-mer comprising of the DNA-sequence 5'TACCACTACAATGGATG-3'. (SEQ ID NO:1)

The sequences of the apoptin-associating cDNAs were compared with known gene sequences from EMBL/Genbank.

Construction of pMAL-AAP-1 and pET22b-AAP-1

For the construction of the protein overexpression plasmids, which enable the production and isolation of apoptin-associated protein, plasmids pMALTB and pET22b were used. Plasmid pMALTB is a derivative of pMAL-C2 (New England Biolabs) in which the factor Xa site has been replaced by a Trombin site. Plasmid pMALTB was treated with BamHI and SalI and the ±7.0 kb DNA fragment was isolated from an agarose/TBE gel (QIAGEN® gel extraction kit). The AAP-1 sequence encoding the complete open reading frame was obtained by a PCR reaction on pACT-AAP-1b with the forward primer: 5' AACGGGATCCG-GCGGCATGGGCGACAAGAAGAGCCCGACC 3' (SEQ ID NO:7) and the reversed primer: 5' AAAAGTCGACT-CAGAAAGATTCATCATTGACTGCTGACAT 3'; (SEQ ID NO:8) the ±0.7 kb PCR fragment was digested with BamHI and SalI and isolated from an agarose/TBE gel (QIAGEN® gel extraction kit). The final construct containing a fusion between the MBP gene and the AAP-1 gene under the regulation of the IPTG inducible tac promoter was called pMAL-AAP-1.

Plasmid pET22b (Novagen) was treated with NdeI and NotI and the ±5.5 kb DNA fragment was isolated from an agarose/TBE gel (QIAGEN® gel extraction kit). The AAP-1 sequence encoding the open reading frame was obtained by a PCR reaction on pACT-AAP-1b with the forward primer: 5' GGGAATTCCATATGGGCGACAAGAA-GAGCCCGACC 3' (SEQ ID NO:9) and the reversed primer: 5' AAGGAAGTACGCGGCCGCGAAAGAT-TCATCATTGACTGCTGACATGT 3'; (SEQ ID NO:10) the PCR product was treated with NdeI and NotI and the ±0.7 kb fragment was isolated from an agarose/TBE gel (QIAGEN® gel extraction kit). The final construct containing a fusion between the AAP-1 gene and the (His)6-tail under the regulation of the IPTG inducible T7lac promoter was called pET22b-AAP-1.

Both constructs were proven to be correct by restriction-enzyme analysis and DNA-sequencing according to the Sanger method (1977).

All cloning steps were essentially carried out as described by Maniatis et al. (1992).

Bacterial Strains for Overexpression of MBP-AAPI and AAP-1-(His)6

For protein production with the plasmid pMAL-AAP-1 the *E. coli* strain B834(□DE3) was used and for the plasmid pET22b-AAP-1 the *E. coli* strain BL21(DE3) was used. Both strains were obtained from Novagen.

Apoptin induces specifically apoptosis in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

The following examples are offered by way of illustration of the present invention, not limitation.

Example 1

Construction of a Bait Plasmid Expressing a Fusion Gene Product of GAL4-DNA-Binding Domain and Apoptin To examine the existence of apoptin-associating proteins in the human transformed/tumorigenic cDNA library, a so-called bait plasmid had to be constructed. To that end, the complete apoptin-encoding region, flanked by about 40 basepairs downstream from the apoptin gene, was cloned in the multiple cloning site of plasmid pGBT9.

The final construct, called pGBT-VP3, was analyzed by restriction-enzyme analysis and sequencing of the fusion area between apoptin and the GAL4-DNA-binding domain.

Example 2

A Gene (Fragment) Encoding an Apoptin-Associating Protein is Determined by Transactivation of a GAL4-Responsive Promoter in Yeast The apoptin gene is fused to the GAL4-DNA-binding domain of plasmid pGBT-VP3, whereas all cDNAs derived from the transformed human B cells are fused to the GAL4-activation domain of plasmid pACT. If one of the proteinaceous substances encoded by said cDNAs binds to apoptin, the GAL4-DNA-binding domain will be in the vicinity of the GAL4-activation domain resulting in the activation of the GAL4-responsive promoter, which regulates the reporter genes HIS3 and LacZ.

The yeast clones containing plasmid expressing apoptin and a plasmid expressing an apoptin-associating protein fragment can grow on a histidine-minus medium and will stain blue in a beta-galactosidase assay. Subsequently, the plasmid with the cDNA insert encoding the apoptin-associating protein can be isolated and characterized.

Before we could do so, however, we have determined that transformation of yeast cells with pGBT-VP3 plasmid alone, or in combination with an empty pACT vector, did not result in the activation of the GAL4-responsive promoter.

Example 3

Identification of Apoptin-Associating Proteins Encoded by cDNAs Derived from a Human Transformed B Cell Line We have found two yeast colonies, which upon transformation with pGBT-VP3 and pACT-cDNA were able to grow on histidine-minus medium (also lacking leucine and tryptophan) and stained blue in a beta-galactosidase assay. These results indicate that the observed yeast colonies contain, besides the bait plasmid pGBT-VP3, also a pACT plasmid encoding a potential apoptin-associating protein.

Plasmid DNA was isolated from the positive yeast colony, which was transformed in bacteria. By means of a filter-hybridization assay using a pACT-specific labeled DNA-probe, the clones containing pACT plasmid could be determined. Subsequently, pACT DNA was isolated and digested with restriction enzyme XhoI, which is indicative for the presence of a cDNA insert. Finally, the pACT plasmids containing a cDNA insert was sequenced by using the Sanger method (Sanger et al., 1977).

Example 4

Description of Apoptin-Associating Proteins

The yeast genetic screen for apoptin-associating proteins resulted in the detection of two cDNA clones A and B comprising a single type of protein, namely a novel protein called apoptin-associating protein 1, abbreviated as AAP-1. The cDNA AAP-1-b (SEQ. ID NO:5) harbors the complete open reading frame with an ATG-initiation codon, whereas the AAP-1-a(SEQ. ID NO:4) cDNA sequence contains a partial AAP-1 open reading frame, which is completely homologous to the AAP-1-b DNA sequence.

The determined DNA sequence of the AAP-1-a and AAP-1-b cDNA clones are shown in FIGS. 1 and 2, respectively. The amino acid sequence, derived from the detected DNA sequence of clone AAP-1-b, which represents the complete AAP-1 a.a. sequence, is given in FIG. 3 (SEQ. ID NO:6).

Example 5

Construction of an Expression Vector for the Identification of AAP-1 Protein in Mammalian Cells To study whether the cloned cDNAs AAP-1-a and AAP-1-b indeed encode (apoptin-associating) protein products, we have carried out the following experiments.

The DNA plasmid pMT2SM contains the adenovirus 5 major late promoter (MLP) and the SV40 ori enabling high levels of expression of foreign genes in transformed mammalian cells, such as SV-40-transformed Cos cells.

Furthermore, the pMT2SM vector contains a Myc-tag (amino acids: EQKLISEEDL) (SEQ ID NO:2) which is in frame with the foreign-gene product. This Myc-tag enables the recognition of, e.g., apoptin-associating proteins by means of the Myc-tag-specific 9E10 antibody.

The pMT2SM vectors expressing Myc-tagged AAP-1-a or AAP-1-b cDNAs were constructed as follows. The pACT-AAP-1-a and pACT-AAP-1-b cDNA clones were digested with the restriction enzyme XhoI and the cDNA inserts were isolated. The expression vector pMT2SM was digested with XhoI and treated with calf intestine alkaline phosphatase and ligated to the isolated AAP-1 cDNA inserts. By sequence analysis, the pMT2SM constructs containing the AAP-1-a or AAP-1-b cDNA in the correct orientation were identified.

The synthesis of Myc-tagged AAP-1 protein was analyzed by transfection of Cos cells with plasmid pMT2SM-AAP-1-a or pMT2SM-AAP-1-b. As negative control, Cos cells were mock-transfected. Two days after transfection, the cells were lysed and Western-blot analysis was carried out using the Myc-tag-specific antibody 9E10.

The Cos cells transfected with pMT2SM-AAP-1-a and pMT2SM-AAP-1-b were proven to synthesize a specific Myc-tagged AAP-1 product with the expected size of approximately 33 kDa (AAP-1-a) or 35 kDA (AAP-1-b). As expected, the lysates of the mock-transfected Cos cells did not contain a protein product reacting with the Myc-tag-specific antibodies.

These results indicate that we have been able to isolate cDNAs that are able to produce a protein product with the ability to associate to the apoptosis-inducing protein apoptin.

Example 6

Co-Immunoprecipitation of Myc-Tagged AAP-1 Protein with Apoptin in a Transformed Mammalian Cell System Next, we have analyzed the association of apoptin and the AAP-1 protein by means of co-immunoprecipitations using the Myc-tag-specific antibody 9E10. The 9E10 antibodies were shown not to bind directly to apoptin, which enables the use of 9E10 for carrying out co-immuno-precipitations with (myc-tagged) apoptin-associating proteins and apoptin.

To that end, Cos cells were co-transfected with plasmid pCMV-VP3 encoding apoptin and with plasmid pMT2SM-AAP-1-a. As a negative control, cells were transfected with pCMV-VP3 expressing apoptin and a plasmid pcDNA3. 1. LacZ-myc/His-LacZ encoding the myc-tagged beta-galactosidase, which does not associate with apoptin.

Two days after transfection, the cells were lysed in a buffer consisting of 50 mM Tris (PH 7.5), 250 mM NaCl, 5 mM EDTA, 0.1% TRITON X100, 1 mg/ml $Na_4P_2O_7$ and freshly added protease inhibitors such as PMSF, Trypsine-inhibitor, Leupeptine and $Na_3VO_4$. The specific proteins were immuno-precipitated as described by Noteborn et al. (1998) using the Myc-tag-specific antibodies 9E10, and analyzed by Western blotting.

Staining of the Western blot with 9E10 antibodies and 111.3 antibodies, which are specifically directed against myc-tag and apoptin, respectively, showed that the "total" cell lysates contained apoptin and the Myc-tagged AAP-1 protein or beta-galactosidase product. Immunoprecipitation of the Myc-tagged AAP-1 products was accompanied by the immuno-precipitation of apoptin product of 16 kDa. In contrast, immunoprecipitation of myc-tagged beta-galactosidase did not result in a significant co-precipitation of the apoptin protein.

In total, three independent immunoprecipitation experiments were carried out, which all showed the associating ability of apoptin to the AAP-1 protein.

These results indicate that the novel determined AAP-1 protein is able to specifically associate with apoptin not only in the yeast background, but also in a mammalian transformed cellular system.

Example 7

Over-Expression of the Novel AAP-1 Protein in Human Transformed Cells Induces the Apoptotic Process In addition, we have examined whether AAP-1 carries apoptotic activity. First, we have analyzed the cellular localization of the novel AAP-1 protein in human transformed cells. To that end, the human osteosarcoma-derived Saos-2 cells were transfected, as described by Danen-van Oorschot (1997), with plasmid pMT2SM-AAP-1-a or pMT2SM-AAP-1-b encoding the myc-tagged AAP-1-a or AAP-1-b protein, respectively.

By indirect immunofluorescence using the myc-tag-specific antibody 9E10 and DAPI, which stains the nuclear DNA, it was shown that both the partial and complete AAP-1 protein were present in the nucleus of the cell. Actually, it co-localizes with the chromatin/DNA structures.

Finally, we examined whether (over)-expression of both cDNAs encoding complete or partial AAP-1 protein results in induction of apoptosis. Four days after transfection, the majority of AAP-1-positive cells were aberrantly stained with DAPI, which is indicative for induction of apoptosis (Telford, 1992, Danen-van Oorschot, 1997).

Co-expression of apoptin and both AAP-1 proteins in human tumor cells, such as Saos-2 cells, results in an apoptotic process faster than expression of apoptin or AAP-1 protein alone. The results of the apoptotic activity of the complete AAP-1 protein are shown in FIG. 4.

The fact that AAP-1 protein can induce apoptosis in p53-minus Saos-2 cells indicates that AAP-1 can induce p53-independent apoptosis. These results imply that AAP-1 can be used as an anti-tumor agent in cases where other (chemo)therapeutic agents will fail. Furthermore, the finding that both apoptin and AAP-1 induce a p53-independent pathway indicates that AAP-1 fits in the apoptin-induced apoptotic pathway.

Example 8

Co-Localization of Apoptin and AAP-1 in Human Tumor Cells

To establish the possible co-localization of apoptin and AAP-1 in transformed human cells, plasmids encoding apoptin and AAP-1 were transfected in Saos-2 cells. Expression of AAP-1 and apoptin was monitored by indirect immunofluorescence by means of a confocal-laser scanning microscopy with the use of specific antibodies mAb myc 9E10 against the myc-tag on AAP-1 and pAb VP3-c against the C-terminus of apoptin.

Cells co-transfected with a plasmid encoding AAP-1 and a plasmid encoding apoptin expressed these proteins predominantly in the nucleus. Both, apoptin and AAP-1 had granular structures and the above described characteristic structures. By means of confocal-laser scanning microscopy, partial co-localization of AAP-1 and apoptin was clearly shown to occur in these nuclear structures.

In conclusion, we have identified an apoptin-associating protein, namely the novel AAP-1 protein, which is present in the nucleus and able to induce (p53-independent) apoptosis in human tumor cells. Furthermore, when AAP-1 and apoptin are expressed in the same cell the two apoptosis inducing proteins are co-localizing in the nucleus of human tumor cells.

Example 9

AAP-1 Localizes in Human Normal Diploid Cells in Cytoplasmic Structures

Next, we have examined whether AAP-1 behaves similar in normal human diploid non-transformed cells as has been found for AAP-1 in human tumor cells.

To that end, human diploid VH10 fibroblasts (Danen-Van Oorschot, 1997) were transfected using FUGENE® according the protocol of the supplier (Roche, Almere, The Netherlands), with plasmid pMT2SM-AAP-1b encoding the myc-tagged complete AAP protein. In parallel, human tumor-derived Saos-2 cells were also transfected with plasmid pMT2SM-AAP-1-b.

By indirect immunofluorescence using the myc-tag-specific antibody 9E10, it was shown that in normal diploid VH10 fibroblasts AAP-1 protein is located in the cytoplasm. As expected, in the human tumor Saos-2 cells AAP-1 is located in the nucleus.

Furthermore, we have examined the effect of co-expression of AAP-1 and apoptin in human VH10 fibroblasts on the cellular localization of AAP-1, as described for cells expressing AAP-1 alone. The immunofluorescence data show that both apoptin and AAP-1 are located in cytoplasmic structures. These findings indicate that AAP-1 and/or apoptin expression do not result in the nuclear localization of one or the other in normal (human) diploid cells.

Example 9

Co-Localization of Apoptin and AAP-1 in Human Fibroblasts

To establish the possible co-localization of apoptin and AAP-1 in non-transformed cells, plasmids encoding apoptin and AAP-1 were transfected in VH10 cells. Expression of AAP-1 and apoptin were monitored by indirect immunofluorescence by means of a confocal-laser scanning microscopy with the use of specific antibodies mAb myc 9E10 against the myc-tag on AAP-1 and pAb VP3-c against the C-terminus of apoptin. Cells were screened for (co-) localization of apoptin and AAP-1 and for induction of apoptosis by nuclear staining with DAPI.

Cells co-transfected with a plasmid encoding AAP-1 and a plasmid encoding apoptin expressed these proteins predominantly in the cytoplasm. Apoptin and AAP-1 both had a thready and sometimes granular structure. By means of confocal-laser scanning microscopy, co-localization of AAP-1 and apoptin was clearly shown to occur in these cytoplasmic structures. Similar cytoplasmic structures were observed with AAP-1, when expressed alone or vice versa when apoptin was expressed alone.

Thus, in the presence or absence of apoptin, AAP-1 has a cytoplasmic localization and thready-aggregated structures in non-transformed human fibroblasts.

In conclusion, we have identified an apoptin-associating protein, namely AAP-1, which is differentially located in human diploid non-transformed cells versus human tumorigenic cells. These results show that AAP-1 functions in a different way in normal diploid cells as in tumorigenic cells. Furthermore, when ADP-1 and apoptin are expressed in the same normal non-transformed cell the two apoptosis inducing proteins are co-localizing in the cytoplasm.

Example 10

The Effect on Induction of Covalent Linkage of an SV40 Large T Antigen Nuclear Localization Signal to the Apoptin Protein In the following experiments, we have examined whether expression of a chimeric protein consisting of apoptin and the nuclear localization signal of SV40 LT antigen (amino acids N-terminal-Proline-Proline-Lysine-Lysine-Lysine-Arginine-Lysine-Valine-C-terminal (SEQ. ID NO:7) of SV40 large T antigen covalently linked to the N-terminus of apoptin) results in the induction of apoptosis in non-transferred and transformed human cells. The chimeric protein is called NLS-apoptin.

To that end, non-transformed VH10 human fibroblasts and transformed human osteosarcoma-derived Saos-2 cells (Danen-van Oorschot et al., 1997) were transfected with a plasmid encoding the chimeric protein NLS-apoptin. In transformed human cells, expression of NLS-apoptin resulted in the nuclear localization of apoptin and induction of apoptosis. Expression of NLS-apoptin in normal human fibroblasts, however, resulted in the nuclear localization of apoptin, but not in induction of apoptosis. This indicates that "forcing" of transporting apoptin into the nucleus does not result in its apoptotic activity per se. Apoptin seems to require an additional tumor-related event.

Example 11

The Effect of Expression of NLS-Apoptin on AAP-1 in Normal Human Fibroblasts

Next, we have examined whether the expression of NLS-apoptin can influence the cellular location of AAP-1 and/or its apoptotic activity in normal human fibroblasts. To that end, VH10 cells were co-transfected with plasmids encoding NLS-apoptin or AAP-1. By means of indirect-immunofluorescence and DAPI-staining using a fluorescence microscopy, it was clearly established that both NLS-apoptin and AAP-1 were located in the nucleus without inducing apoptosis. This indicates that "forcing" of transporting AAP-1 through NLS-apoptin into the nucleus does not result in AAP-1 apoptotic activity per se. AAP-1 like apoptin seems to require an additional tumor-related event to become apoptotic in the nucleus of transformed cells.

Example 12

AAP-1 does not Induce Apoptosis in Human Diploid Non-Transformed Cells

In the following experiments we have examined whether AAP-1 alone or in combination with apoptin is also able to induce apoptosis in human diploid non-transformed fibroblasts as has been observed for human tumorigenic/transformed cells.

To that end, VH10 cells were transfected with plasmid pMT2SM-AAP-1-b as described above. The transfected cells were analyzed by indirect immunofluorescence using the myc-tag-specific and/or apoptin-specific antibodies and DAPI-staining. DAPI stains intact DNA in a different way that apoptotic DNA (Telford et al., 1992). The analysis clearly shows that VH10 fibroblasts containing AAP-1 protein alone or both AAP-1 and apoptin do not undergo apoptosis.

The obtained results show that apoptin-related proteins such as AAP-1 might behave in a different way in "healthy" cells in comparison to tumor cells.

Example 13

Diagnostic Assay for Cancer Cells

Based on the present report, we can conclude that the cellular localization of AAP-1 is different in tumorigenic/transformed human cells in comparison to normal human non-transformed cells. Furthermore, accumulation of AAP-1 in the nucleus correlates with apoptosis induction, whereas cytoplasmic localization correlates with cell viability and normal proliferative capacity. Therefore, we are able to develop a diagnostic assay for the identification of (human) cancer cells versus normal "healthy" non-transformed cells.

The assay consists of transfecting "suspicious" (human) cells, for instance from human origin, with a plasmid encoding AAP-1, or infecting the cells with viral vectors expressing AAP-1. Subsequently, the cells will be examined, 1) for the ability to undergo apoptosis by the over-expressing AAP-1 gene and 2) for a shift in the localization of AAP-1 from the cytoplasm to the nucleus.

The intracellular localization of AAP-1 can be determined, using an immunofluorescence assay with monoclonal antibodies specific for AAP-1 and/or specific for a tag linked to AAP-1 such as the herein described myc-tag. If the percentage of apoptosis and/or the nuclear localization of AAP-1 in the analyzed cells expressing AAP-1 is significantly higher than in AAP-1-positive control "healthy" cells, one can conclude that the analyzed cells have become tumorigenic/transformed. As a positive control, known human tumorigenic cells will be used for expressing AAP-1.

Example 14

Co-Expression of SV40 Large T Antigen and AAP-1 Results in Translocation of AAP-1 and Induction of Apoptosis We have examined the effect of expression of transforming genes on AAP-1-induced apoptosis in normal human cells derived from healthy individuals. To that end, human VH10 diploid fibroblasts were transiently co-transfected with plasmid pMT2SM-AAP-1-b encoding the complete AAP-1 protein and either plasmid pR-s884 encoding SV40 large T antigen, or the negative-control plasmid pCMV-neo (Noteborn and Zhang, 1998).

By indirect immunofluorescence, the cells were analyzed for AAP-1-induced apoptosis. The normal VH10 cells did not undergo apoptosis when AAP-1 was transfected with the negative-control plasmid. The results showed, as expected, that expression of AAP-1 is not able to induce apoptosis in normal human diploid cells, confirming the above mentioned data. However, normal diploid human fibroblasts expressing both AAP-1 and SV40 large T antigen underwent AAP-1-induced apoptosis.

The transition of normal human cells, from AAP-1-resistance to AAP-1-susceptibility, can probably be explained by the fact that the AAP-1 protein translocates from a cytoplasmic localization to a nuclear localization. This transition becomes apparent already 2 days after transfection of plasmids encoding the transforming protein SV40 large T antigen. One can conclude that an event takes place, in this example due to expression of a transforming product derived from a DNA-tumor virus, which results in the translocation of over-expressed AAP-1 from the cytoplasm to the nucleus, which is followed by induction of apoptosis.

Example 15

Diagnostic Assay for Cancer-Inducing Genes, Agents and Cancer-Process based on AAP-1-Induced Apoptosis Based on the present report, we are able to develop a diagnostic assay for the identification of cancer-inducing and/or transforming agents or genes.

A first type of assay consists of transfecting "normal" cells, for instance from human origin, with a plasmid encoding AAP-1, or infecting the cells with viral vectors expressing AAP-1, together with a plasmid encoding a putative transforming/cancer-inducing gene. Subsequently, the cells will be examined, 1) for the ability to undergo apoptosis by the over-expressing AAP-1 gene and 2) for a shift in the localization of AAP-1 from the cytoplasm to the nucleus.

The intracellular localization of AAP-1 can be determined, using an immunofluorescence assay with monoclonal antibodies specific for AAP-1 and/or specific for a tag linked to AAP-1 such as the herein described myc-tag. If the percentage of apoptosis and/or the nuclear localization of AAP-1 in normal cells co-expressing AAP-1 and the putative transforming/cancer-inducing gene is significantly higher than in AAP-1-positive control cells expressing a control plasmid, one can conclude that the analyzed gene indeed has transforming/cancer-inducing activity.

A second example of a diagnostic test is based on the treatment of cultured normal diploid cells with a putative carcinogenic agent. The agent can be added, for instance, to the culture medium for various lengths of time. Subsequently, the cells are transfected with a plasmid encoding AAP-1. This approach can also be carried out by first transfecting/infecting the normal diploid cells, and then treating the cells with the agent to be tested.

The subsequent steps of the assay are the same as described for the in this section described first type of diagnostic assay. If the percentage of apoptosis and/or the nuclear localization of AAP-1 in normal cells expressing AAP-1 and the putative carcinogenic agent is significantly higher than in AAP-1-positive control cells expressing a control agent, one can conclude that the analyzed agent indeed has transforming/cancer-inducing activity.

A third example of a diagnostic test is based on the treatment of cultured normal diploid cells derived from a skin biopsy of the potential cancer-prone individual to be tested and cultured in suitable medium. Next, the cells are irradiated with UV and subsequently transfected with a plasmid encoding AAP-1, or infected with a viral vector expressing AAP-1, or the cells are first transfected/infected and then irradiated. In parallel, diploid cells from a normal healthy individual will be used as control.

The subsequent steps of the assay are the same as described for the first type of diagnostic assay. If after UV-treatment the percentage of apoptosis and/or the nuclear localization of AAP-1 in diploid cells derived from the potential cancer-prone individual is significantly higher than in UV-treated AAP-1-positive control cells, one can conclude that the analyzed individual is cancer-prone.

Example 16

AAP-1 and YY1 Associate with Each Other in Transformed Cells

The mouse homologue of AAP-1, RYBP (Garcia et al., 1999) can interact with YY1. YY1 can activate or repress the transcription of cellular and viral proteins. Protein—protein interactions can influence the activity of YY1. AAP-1 might interact with YY1. The interaction between AAP-1 and YY1 could influence the activity of YY1, resulting in transcriptional repression or activation. Transcription of genes could be important for the apoptotic activity of apoptin and/or AAP-1.

To establish whether AAP-1 forms a complex with YY1 in vitro, plasmids encoding AAP-1 and YY1 (pCMV-HAVY-1; Kind gift of Dr Yang Shi, Harvard Medical School, Boston, USA) were co-transfected in Cos-cells. As a negative control, YY-1 was co-expressed with LacZ. The cells were lysed and an immunoprecipitation assay was performed with the use of specific antibodies against the myc-tag of AAP-1 (or LacZ), anti-myc 9E10, and against YY1, anti-YY1. The resulting complexes were analyzed by Western-blotting techniques. In the cell-lysates, AAP-1 and/or YY1 and/or LacZ were detected, as expected.

In cells transfected with AAP-1 and YY1 it was clearly visible that when we performed an immunoprecipitation with antibodies specific for myc-tagged AAP-1, both AAP-1 and YY1 were detectable. The blot showed a band at 32 kDa (AAP-1) and a band at 67 kDa (YY1). Additionally, we performed an immunoprecipitation using specific antibodies for YY1. Again, both YY1 and AAP-1 were detectable on the Western blot.

In cells transfected with a plasmid expressing only AAP-1, only AAP-1 could be detected. Cells transfected with a plasmid encoding YY1 showed expression of YY1, AAP-1 was not detected. To rule out a non-specific binding of AAP-1 with YY1, cells were transfected with AAP-1 and LacZ and immunoprecipitations were carried out with antibodies specific for LacZ. Although, LacZ protein was clearly visible on the Western Blot, no AAP-1 protein was visible.

Therefore, the obtained results show that AAP-1 specifically binds to the transcription-related factor YY1.

Example 17

Production and Isolation of MBP-AAP-1 and AAP-1-(His)6

To examine the possibility of MBP-AAP-1 and AAP-1-(His)6 fusion protein production the AAP-1 nucleic acid coding for the open reading frame was cloned in the protein overexpression cassettes pMALTB and pET22b. Inducing the E. coli cells according to the manufactures instructions (Novagen) leads to the production of soluble fusion protein.

Isolation of the MBP AAP-1 fusion protein via affinity chromatography (amylose resin, New England Biolabs) and ion exchange chromatography (High-S, BIORAD®) leads to a 90 to 95% pure, full length protein. Size exclusion chromatography (AMERSHAM® SUPEROSE®6 HR 10/30) of this protein shows that a substantial part of the MBP-AAP-1 preparation appears to behave as one distinct species, a Homotrimer or Homo-tetramer. This finding would suggest that recombinant AAP-1 (in the form of a MBP fusion protein) is capable of assuming a correct fold and is likely to be biologically active.

Isolation of the AAP-1-(His)6 protein with metal affinity chromatography (Ni$^{2+}$-NTA, QIAGEN®) leads to a ±80% pure protein batch.

In conclusion, fusion of AAP-1 to MBP results in properly folded, soluble AAP-1 which is likely to be biologically active.

Example 18

Production of Polyclonal Antibodies Directed Against AAP-1 Proteins

For the production of polyclonal antibodies against AAP-1 proteins a putative immunogenic peptide was synthesized (AAP-1 peptide consists of the amino acids N/terminus-CTKTSETNHTSRPRLK-C/terminus; EUROGENTEC® SA, Belgium). (SEQ ID NO:3) Subsequently, rabbits were injected with the specific peptides according the standard procedures of the manufacturer.

The serum derived from the rabbits injected with the AAP-1 peptide was shown to be specific for the above described AAP-1 products by means of ELISA and Western-blot assays. These results imply that we have generated specific antibodies, which can be used for detecting the apoptin-associating protein AAP-1.

In conclusion, we have provided evidence that interference of specific factors with the function of AAP-1 proteins results in induction of apoptosis.

Therapies based on induction of (p53-independent) apoptosis are possible utilizing the interference with the function of AAP-1 proteins. An example of such an interfering factor is apoptin. Another CAV-derived protein, which is known to induce apoptosis and also known to enhance apoptin activity is VP2 (Noteborn et al., 1997).

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

REFERENCES

1. Bellamy, C. O. C., Malcomson, R. D. G., Harrison, D. J., and Wyllie, H. 1995. Cell death and disease: The biology and regulation of apoptosis. Seminars in Cancer Biology 6, 3–12.
2. Danen-Van Oorschot, A. A. A. M., Fischer, D. F., Grimbergen, J. M., Klein, B., Zhuang, S.-M., Falkenburg, J. H. F., Backendorf, C., Quax, P. H. A., Van der Eb, J. A., and Noteborn, M. H. M. (1997). Apoptin induces apoptosis in human transformed and malignant cells but not in normal cells. Proceedings National Academy Sciences, USA: 94, 5843–5847.
3. Danen-Van Oorschot, A. A. A. M, Den Hollander, A., Takayama, S., Reed, J., Van der Eb, A. J. and Noteborn, M. H. M. (1997a). BAG-1 inhibits p53-induced but not apoptin-induced apoptosis. Apoptosis 2, 395–402.
4. Duke, R. C., Ocjius, D. M., Young, J, D-E. (1996). Cell suicide in health and disease. Scientific American December 1996, 48–55.
5. Durfee, T., Becherer, K., Chen, P.-L., Yeh, S.-H., Yang, Y., Kilburn, A. E., Lee, W.-H., and Elledge, S. J. (1993). The retinoblastoma protein associates with the protein phosphate type I catalytic subunit. Genes and Development 7, 555–569.
6. Earnshaw, W. C., 1995. Nuclear changes in apoptosis. Current Opinion in Cell Biology 7, 337–343.
7. Fields, S. and Song, O. K. (1989). A novel genetic system to detect protein—protein interactions. Nature 340, 245–246.
8. Garcia, E., Marcos-Gutierrez, C., Del Mar Lorente, M., Moreno, J. C., and Vidal, M. RYBP, a new repressor protein that interacts with components of the mammalian polycomb complex, and with the transcription factor YY1. (1999). EMBO Journal 18, 3404–3418.

9. Hockenberry, D. M. (1994). Bcl-2 in cancer, development and apoptosis. Journal of Cell Science, Supplement 18, 51–55.
10. Hoffman, C. S. and Winston, F. (1987). A ten-minute DNA preparation from yeast efficiently releases autonomous plasmids for transformation of *Escherichia coli*. Gene 57, 267–272.
11. Kerr, J. F. R., Winterford, C. M., and Harmon, B. V. (1994). Apoptosis: Its significance in cancer and cancer therapy. Cancer 73, 2013–2026.
12. Klebe, R. J., Harriss, J. V., Sharp, Z. D., and Douglas, M. G. (1983). A general method for polyethylene-glycol-induced genetic transformation of bacteria and yeast. Gene 25, 333–341.
13. Levine, A. J. (1997). p 53, the cellular gatekeeper for growth and division. Cell 88, 323–331.
14. Maniatis, T., Fritsch, E. F., and Sambrook, J. (1982). Molecular Cloning: A Laboratory Manual. CSHL Press, New York, USA.
15. McDonell T. J., Meyn, R. E., Robertson, L. E. (1995). Implications of apoptotic cell death regulation in cancer therapy. Seminars in Cancer Biology 6, 53–60.
16. Noteborn, M. H. M. (1996). PCT application WO 96/41191. Apoptin induces apoptosis in human transformed and malignant cells but not in normal cells as essential characteristic for the development of an anti-tumor therapy.
17. Noteborn, M. H. M., and De Boer, G. F. (1996). Patent USA/no. 030, 335.
18. Noteborn, M. H. M., DeBoer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
19. Noteborn, M. H. M., and Pietersen, A. (1998). A gene delivery vehicle expressing the apoptosis-inducing proteins VP2 and/or apoptin. PCT Application no. PCT/NL98/00213.
20. Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. Journal of Virology 68, 346–351.
21. Noteborn, M. H. M., Verschueren, C. A. J., Koch, G., and Van der Eb, A. J. (1998). Simultaneous expression of recombinant baculovirus-encoded chicken anemia virus (CAV) proteins VP1 and VP2 is required for formation of the CAV-specific neutralizing epitope. Journal General Virology, 79, 3073–3077.
22. Noteborn, M. H. M., and Zhang, Y. (1998). Methods and means for determining the transforming capability of agents, for determining the predisposition of cells to become transformed and prophylactic treatment of cancer using apoptin-like activity. PCT Application no. PCT/NL98/00457.
23. Noteborn, M. H. M., Danen-van Oorschot, A. A. A. M., Van der Eb, A. J. (1998a). Chicken anemia virus: Induction of apoptosis by a single protein of a single-stranded DNA virus. Seminars in Virology 8, 497–504.
24. Paulovich, A. G., Toczyski, D., Hartwell, H. (1997). When checkpoints fail. Cell 88, 315–321.
25. Pietersen, A. M., Van der Eb, M. M., Rademaker, H. J., Van den Wollenberg, D. J. M., Rabelink, M. J. W. E., Kuppen, P. J. K., Van Dierendonck, J. H., Van Ormondt, H., Masman, D., Van de Velde, C. J. H., Van der Eb, Hoeben, R. C., and Noteborn, M. H. M. (1998). Specific tumor-cell killing with adenovirus vectors containing the apoptin gene. Gene Therapy 6, 882–892.
26. Rose, M. D., Winston, F., and Hieter, P. (1990). Methods in yeast genetics. A laboratory course manual. Cold Spring Harbor Laboratory Press, Cold Spring Harbor, N.Y., USA.
27. Sachs, L. and Lotem, J. (1993). Control of programmed cell death in normal and leukemia cells: New implications for therapy. Blood 82, 15–21.
28. Sanger, F., Nicklen, S., and Coulsen, A. R. (1977). DNA sequencing with chain-terminating inhibitors. Proceedings National Academic Sciences USA 74, 5463–5467.
29. Steller, H. (1995). Mechanisms and genes of cellular suicide. Science 267, 1445–1449.
30. Telford, W. G., King, L. E., Fraker, P. J. (1992). Comparative evaluation of several DNA binding dyes in the detection of apoptosis-associated chromatin degradation by flow cytometry. Cytometry 13, 137–143.
31. Teodoro, J. G. and Branton, P. E. (1997). Regulation of apoptosis by viral gene products. Journal of Virology 71, 1739–1746.
32. Thompson, C. B. (1995). Apoptosis in the pathogenesis and treatment of disease. Science 267, 1456–1462.
33. White, E. (1996). Life, death, and the pursuit of apoptosis. Genes and development 10, 1–15.
34. Wyllie, A. H. (1995). The genetic regulation of apoptosis. Current Opinion in Genetics and Development 5, 97–104.
35. Wyllie, A. H., Kerr, J. F. R., Currie, A. R. (1980). Cell death: The significance of apoptosis. International Review of Cytology 68, 251–306.
36. Yang, X., Hubbard, E. J. A., and Carlson, M. (1992). A protein kinase substrate identified by the two-hybrid system. Science 257, 680–682.
37. Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 51, 118–120.
38. Zhuang, S.-M., Shvarts, A., Van Ormondt, H., Jochemsen, A.-G., Van der Eb, A. J., Noteborn, M. H. M. (1995). Apoptin, a protein derived from chicken anemia virus, induces a p53-independent apoptosis in human osteosarcoma cells. Cancer Research 55, 486–489.

What is claimed is:

1. An isolated or recombinant nucleic acid sequence encoding an apoptin-associating proteinaceous substance (AAP-1), wherein said AAP-1 comprises amino acid positions 23 to 250 of SEQ ID NO: 6 or a functional fragment thereof, which functional fragment is able to induce apoptosis and which comprises amino acids 54 to 248 of SEQ ID NO: 6.

2. The isolated or recombinant nucleic acid sequence of claim 1, wherein said isolated or recombinant nucleic acid sequence encoding AAP-1 comprises nucleotide positions 142 to 829 of SEQ ID NO: 5, which is able to induce apoptosis.

3. A vector comprising the isolated or recombinant nucleic acid sequence of claim 1.

4. The vector of claim 3 comprising a gene-delivery vehicle.

5. An isolated host cell comprising the isolated or recombinant nucleic acid sequence of claim 1.

6. The host cell of claim 5 wherein said host cell is a yeast cell or a vertebrate cell.

7. A composition comprising the isolated or recombinant nucleic acid sequence of claim 1.

8. The composition of claim 7, wherein said composition induces apoptosis.

9. The composition of claim 8, wherein said apoptosis is p53-independent.

10. An isolated nucleic acid sequence encoding the peptide of SEQ ID NO:6.

* * * * *

SEQUENCE LISTING

<160> NUMBER OF SEQ ID NOS: 7

<210> SEQ ID NO 1
<211> LENGTH: 17

-continued

```
<212> TYPE: DNA
<213> ORGANISM: Artificial
<220> FEATURE:
<223> OTHER INFORMATION: pACT-specific 17-mer

<400> SEQUENCE: 1
taccactaca atggatg                                                    17

<210> SEQ ID NO 2
<211> LENGTH: 10
<212> TYPE: PRT
<213> ORGANISM: Artificial
<220> FEATURE:
<223> OTHER INFORMATION: Myc-tag
<220> FEATURE:
<221> NAME/KEY: SITE
<222> LOCATION: (1)..(10)

<400> SEQUENCE: 2

Glu Gln Lys Leu Ile Ser Glu Glu Asp Leu
1               5                   10

<210> SEQ ID NO 3
<211> LENGTH: 16
<212> TYPE: PRT
<213> ORGANISM: Artificial
<220> FEATURE:
<223> OTHER INFORMATION: AAP-1 Peptide
<220> FEATURE:
<221> NAME/KEY: SITE
<222> LOCATION: (1)..(16)

<400> SEQUENCE: 3

Cys Thr Lys Thr Ser Glu Thr Asn His Thr Ser Arg Pro Arg Leu Lys
1               5                   10                  15

<210> SEQ ID NO 4
<211> LENGTH: 947
<212> TYPE: DNA
<213> ORGANISM: homo sapiens
<220> FEATURE:
<223> OTHER INFORMATION: AAP-1-a nucleic acid
<220> FEATURE:
<221> NAME/KEY: misc_feature
<222> LOCATION: (5)..(5)
<223> OTHER INFORMATION: n can be a, c, g or t
<220> FEATURE:
<221> NAME/KEY: misc_feature
<222> LOCATION: (145)..(145)
<223> OTHER INFORMATION: n can be a, c, g or t

<400> SEQUENCE: 4
accanaccca aaaaagaga tctggaattc ggatcctcga ggccacgaag gccgaaacag       60
tgctgaagcc tttaaatgca gcatctgcga tgtgaggaaa ggcacctcca ccagaaaacc    120
tcggatcaat tctcagctgg tggcncaaca agtggcacaa cagtatgcca ccccaccacc    180
ccctaaaaag gagaagaagg agaaagttga aaagcaggac aaagagaaac ctgagaaaga    240
caaggaaatt agtcctagtg ttaccaagaa aataccaac aagaaaacca aaccaaagtc     300
tgacattctg aaagatcctc ctagtgaagc aaacagcata cagtctgcaa atgctacaac    360
aaagaccagc gaaacaaatc acacctcaag gccccggctg aaaaacgtgg acaggagcac    420
tgcacagcag ttggcagtaa ctgtgggcaa cgtcaccgtc attatcacag actttaagga    480
aaagactcgc tcctcatcga catcctcatc cacagtgacc tccagtgcag ggtcagaaca    540
gcagaaccag ascagctcgg ggtcagagag cacagacaag ggctcctccc gttcctccac    600
```

-continued

```
gccaaagggc gacatgtcag cagtcaatga tgaatctttc tgaaattgca catggaattg    660
tgaaaactat gaatcagggt atgaaattca aaacctccac ctgcccatgc tgcttgcatc    720
cctggagaat cttctgtgga catcgacctc ttagtgatgc tgccaggata atttctgctt    780
gccatgggca tctggccacc aaggaatttc gcaccctgac gattactctt gacacttttaa   840 tgtattccat tgttttatat gattttccta acaatcattt ataattggat gtgctcctga    900
atctactttt tataaaaaaa gccttygtgg cctcgagaga tctatga                  947
```

<210> SEQ ID NO 5
<211> LENGTH: 1131
<212> TYPE: DNA
<213> ORGANISM: Homo sapiens
<220> FEATURE:
<223> OTHER INFORMATION: AAP-1-b nucleic acid

<400> SEQUENCE: 5

```
tataactatc tattcgatga tgaagatacc ccaccaaacc caaaaaaaga gatctggaat     60
tcggatcctc gaggccacga aggcctttct cctccgagcg gcgccggttt cggcttgggg   120
ggggcggggt acagcccatc catgaccatg ggcgacaaga gagcccgac caggccaaaa   180 agacaagcga aacctgccgc agacgaaggg ttttgggatt gtagcgtctg caccttcaga   240
aacagtgctg aagcctttaa atgcagcatc tgcgatgtga ggaaaggcac ctccaccaga   300
aaacctcgga tcaattctca gctggtggca caacaagtgg cacaacagta tgccacccca   360
ccacccccta aaaggagaa gaaggagaaa gttgaaaagc aggacaaaga gaaacctgag   420
aaagacaagg aaattagtcc tagtgttacc aagaaaaata ccaacaagaa aaccaaacca   480
aagtctgaca ttctgaaaga tcctcctagt gaagcaaaca gcatacagtc tgcaaatgct   540
acaacaaaga ccagcgaaac aaatcacacc tcaaggcccc ggctgaaaaa cgtggacagg   600
agcactgcac agcagttggc agtaactgtg ggcaacgtca ccgtcattat cacagacttt   660
aaggaaaaga ctcgctcctc atcgacatcc tcatccacag tgacctccag tgcagggtca   720
gaacagcaga accagagcag ctcggggtca gagagcacag acaagggctc ctcccgttcc   780
tccacgccaa agggcgacat gtcagcagtc aatgatgaat ctttgtgaaa ttgcacatgg   840
aattgtgaaa actatgaatc agggtatgaa attcaaaacc tccacctgcc catgctgctt   900
gcatccctgg agaatcttct gtggacatcg acctcttagt gatgctgcca ggataatttc   960
tgcttgccat gggcatctgg ccaccaagga atttcgcacc ctgacgatta ctcttgacac  1020
ttttatgtat tccattgttt tatatgattt tcctaacaat catttataat tggatgtgct  1080
cctgaatcta ctttttataa aaaggccttc gtggcctcga gagatctatg a           1131
```

<210> SEQ ID NO 6
<211> LENGTH: 352
<212> TYPE: PRT
<213> ORGANISM: Homo sapiens
<220> FEATURE:
<221> NAME/KEY: MISC_FEATURE
<222> LOCATION: (251)..(251)
<223> OTHER INFORMATION: X is an unknown amino acid
<220> FEATURE:
<221> NAME/KEY: MISC_FEATURE
<222> LOCATION: (288)..(289)
<223> OTHER INFORMATION: X is an unknown amino acid
<220> FEATURE:
<221> NAME/KEY: MISC_FEATURE
<222> LOCATION: (314)..(314)
<223> OTHER INFORMATION: X is an unknown amino acid
<220> FEATURE:
<221> NAME/KEY: MISC_FEATURE
<222> LOCATION: (324)..(324)
<223> OTHER INFORMATION: X is an unknown amino acid
<220> FEATURE:
<221> NAME/KEY: MISC_FEATURE
<222> LOCATION: (327)..(327)
<223> OTHER INFORMATION: X is an unknown amino acid
<220> FEATURE:
<221> NAME/KEY: MISC_FEATURE
<222> LOCATION: (352)..(352)
<223> OTHER INFORMATION: X is an unknown amino acid
<400> SEQUENCE: 6

```
His Glu Gly Leu Ser Pro Ser Gly Ala Gly Phe Gly Leu Gly Gly
1               5                   10                  15

Ala Gly Tyr Ser Pro Ser Met Thr Met Gly Asp Lys Lys Ser Pro Thr
            20                  25                  30

Arg Pro Lys Arg Gln Ala Lys Pro Ala Ala Asp Glu Gly Phe Trp Asp
        35                  40                  45

Cys Ser Val Cys Thr Phe Arg Asn Ser Ala Glu Ala Phe Lys Cys Ser
    50                  55                  60

Ile Cys Asp Val Arg Lys Gly Thr Ser Thr Arg Lys Pro Arg Ile Asn
65                  70                  75                  80

Ser Gln Leu Val Ala Gln Val Ala Gln Gln Tyr Ala Thr Pro Pro
                85                  90                  95

Pro Pro Lys Lys Glu Lys Lys Glu Lys Val Glu Lys Gln Asp Lys Glu
            100                 105                 110

Lys Pro Glu Lys Asp Lys Glu Ile Ser Pro Ser Val Thr Lys Lys Asn
        115                 120                 125

Thr Asn Lys Lys Thr Lys Pro Lys Ser Asp Ile Leu Lys Asp Pro Pro
    130                 135                 140

Ser Glu Ala Asn Ser Ile Gln Ser Ala Asn Ala Thr Thr Lys Thr Ser
145                 150                 155                 160

Glu Thr Asn His Thr Ser Arg Pro Arg Leu Lys Asn Val Asp Arg Ser
                165                 170                 175

Thr Ala Gln Gln Leu Ala Val Thr Val Gly Asn Val Thr Val Ile Ile
            180                 185                 190

Thr Asp Phe Lys Glu Lys Thr Arg Ser Ser Ser Thr Ser Ser Ser Thr
        195                 200                 205

Val Thr Ser Ser Ala Gly Ser Glu Gln Gln Asn Gln Ser Ser Ser Gly
    210                 215                 220

Ser Glu Ser Thr Asp Lys Gly Ser Ser Arg Ser Ser Thr Pro Lys Gly
225                 230                 235                 240

Asp Met Ser Ala Val Asn Asp Glu Ser Phe Xaa Asn Cys Thr Trp Asn
                245                 250                 255

Cys Glu Asn Tyr Glu Ser Gly Tyr Glu Ile Gln Asn Leu His Leu Pro
            260                 265                 270

Met Leu Leu Ala Ser Leu Glu Asn Leu Leu Trp Thr Ser Thr Ser Xaa
        275                 280                 285

Xaa Cys Cys Gln Asp Asn Phe Cys Leu Pro Trp Ala Ser Gly His Gln
    290                 295                 300

Gly Ile Ser His Pro Asp Asp Tyr Ser Xaa His Phe Tyr Val Phe His
305                 310                 315                 320

Cys Phe Ile Xaa Phe Ser Xaa Gln Ser Phe Ile Ile Gly Cys Ala Pro
                325                 330                 335

Glu Ser Thr Phe Tyr Lys Lys Ala Phe Val Ala Ser Arg Asp Leu Xaa
            340                 345                 350
```

```
<210> SEQ ID NO 7
<211> LENGTH: 8
<212> TYPE: PRT
<213> ORGANISM: Simian virus 40
<220> FEATURE:
<223> OTHER INFORMATION: SV40 large T antigen

<400> SEQUENCE: 7

Pro Pro Lys Lys Lys Arg Lys Val
1               5
```